United States Patent
Thibault et al.

(10) Patent No.: US 11,348,384 B2
(45) Date of Patent: May 31, 2022

(54) METHOD FOR DETERMINING INDICATORS REGARDING THE POLLUTING NATURE OF MOBILITY TAKING REAL USAGE INTO ACCOUNT

(71) Applicant: IFP Energies nouvelles, Rueil-Malmaison (FR)

(72) Inventors: Laurent Thibault, Lyons (FR); Philippe Degeilh, Fontena y Sous Bois (FR); Gilles Corde, Igny (FR)

(73) Assignee: IFP ENERGIES NOUVELLES, Rueil-Malmaison (FR)

(*) Notice: Subject to any disclaimer, the term of this patent is extended or adjusted under 35 U.S.C. 154(b) by 917 days.

(21) Appl. No.: 16/144,357

(22) Filed: Sep. 27, 2018

(65) Prior Publication Data

US 2019/0102960 A1    Apr. 4, 2019

(30) Foreign Application Priority Data

Sep. 29, 2017 (FR) .................................... 17/59.129

(51) Int. Cl.
*G07C 5/08* (2006.01)
*B60W 40/12* (2012.01)
(Continued)

(52) U.S. Cl.
CPC ........... *G07C 5/0841* (2013.01); *B60W 40/08* (2013.01); *B60W 40/09* (2013.01); *B60W 40/12* (2013.01);
(Continued)

(58) Field of Classification Search
CPC .... G07C 5/0841; G07C 5/008; G07C 5/0808; B60W 40/08; B60W 40/09; B60W 40/12;
(Continued)

(56) References Cited

U.S. PATENT DOCUMENTS 10,747,914 B1 * 8/2020 Hoff .................... G06F 17/10
10,789,396 B1 * 9/2020 Hoff .................... G06F 30/20
(Continued)

FOREIGN PATENT DOCUMENTS

| EP | 2 166 309 A2 | 3/2010 |
| FR | 2 994 923 A1 | 3/2014 |
| FR | 3 049 653 A1 | 10/2017 |

*Primary Examiner* — Sizo B Vilakazi
(74) *Attorney, Agent, or Firm* — Fitch, Even, Tabin & Flannery LLP

(57) ABSTRACT

The invention is a method for determining indicators of pollution from overall mobility of a user, comprising detecting trips in soft modes of transport and trips in motorized vehicles by use of a smart phone; determining a real environmental footprint linked to pollution emissions for each trip in a motorized vehicle by use of a model which estimates pollution emissions by accounting for macroscopic characteristics of the vehicle and a real speed profile representing the style of driving of the user; determining a target environmental footprint from each of the motorized vehicle trips by accounting for a target speed profile representing an optimal style of driving in the model for estimating pollution emissions; and breaking down the environmental footprint for each of the motorized vehicle trips into a footprint linked to the vehicle, and to a style of driving to a type of route and; determining an overall environmental footprint for the mobility of the user by accounting for all trips in soft modes of transport and trips in motorized vehicles over a given time interval, and determining at least one of driving indicators and environmental impact indicators for the user's overall mobility.

20 Claims, 3 Drawing Sheets

(51) Int. Cl.
  *B60W 40/08* (2012.01)
  *G06Q 10/08* (2012.01)
  *G06Q 50/30* (2012.01)
  *B60W 40/09* (2012.01)
  *G01C 21/36* (2006.01)
  *G01N 33/00* (2006.01)
  *G07C 5/00* (2006.01)

(52) U.S. Cl.
  CPC ..... *G01C 21/3697* (2013.01); *G01N 33/0004* (2013.01); *G06Q 10/08* (2013.01); *G06Q 50/30* (2013.01); *G07C 5/008* (2013.01); *G07C 5/0808* (2013.01)

(58) Field of Classification Search
  CPC ............... B60W 50/00; G01C 21/3697; G01N 33/0004; G06Q 10/08; G06Q 50/30; F02D 41/1453; F02D 41/1462; F02D 41/1465; F02D 41/1467; F02D 2041/1433; F02D 2200/1004; F02D 2200/101; F02D 2200/501; F02D 2200/701
  See application file for complete search history.

(56) References Cited

U.S. PATENT DOCUMENTS

| | | | | |
|---|---|---|---|---|
| 2011/0106370 A1* | 5/2011 | Duddle | ................ | G09B 19/16 701/31.4 |
| 2014/0067247 A1* | 3/2014 | Chasse | ................ | B60W 20/10 701/123 |
| 2019/0102509 A1* | 4/2019 | Thibault | ............... | B60W 40/09 |
| 2021/0383486 A1* | 12/2021 | Robinson | ............ | G06F 11/3438 |

* cited by examiner

METHOD FOR DETERMINING INDICATORS REGARDING THE POLLUTING NATURE OF MOBILITY TAKING REAL USAGE INTO ACCOUNT

CROSS REFERENCE TO RELATED APPLICATIONS

Reference is made to French Application No. 17/59.129 filed Sep. 29, 2017, which is incorporated herein by reference in its entirety.

FIELD OF THE INVENTION

The present invention relates to the field of eco-driving, and more generally to that of qualifying the polluting nature of the overall mobility of a user.

DESCRIPTION OF THE PRIOR ART

Currently, improving air quality is a priority for cities. In order to arrive at this, the current prevailing solution is prohibiting certain vehicles deemed to be too polluting from going on the roads (for example, CRIT' AIR stickers). However, for a given vehicle and a given route, pollutant emission levels can vary significantly as a function of the manner in which the vehicle is driven. Although it is real, relatively little is yet known about this impact, as it is still difficult to quantify apart from using extremely expensive laboratory instrumentation.

The Applicant's French patent application FR 3 049 653 describes a method for determining pollutant emissions from a given vehicle using macroscopic parameters for a given route. However, that method only takes trips in a motorized vehicle into account, and not the user's style of driving, and does not allow eco-driving guidance to be generated.

A detailed picture of the prior art regarding models for estimating pollutants is available in patent application FR 3 049 653.

On a large scale, estimating pollutant emissions consists uses coefficients known as "emission factors". The most widely known implementation of this approach is known as COPERT, but that approach does not take real use into account because it concerns mean values for a given vehicle, independently of its use.

In addition, patent application EP 2 166 309 A2, discloses a system which displays the instantaneous pollutant emissions to the driver based on a map or provided directly via the engine control unit. The system described in that application, however, cannot be used to calculate the maximum potential admissible savings, nor to generate eco-driving guidance. In addition, it does not concern a solution which can be deployed on a large scale, because it necessitates measuring emissions from each vehicle (in the case in which a map is used) or connecting to the control units of each vehicle, which is currently impossible.

Regarding eco-driving, the prior art does not provide an approach which takes the air quality into account. An approach which is usually employed accounts for the fuel consumption and/or carbon dioxide consumption such as, for example, in the Applicant's patent application FR 2 994 923, which pertains to a method for determining an energy indicator for a trip in a vehicle and determining an optimal speed which minimizes energy consumption.

The need for tools which can be rolled out on a large scale so that users can take responsibility for their mobility and their driving style still needs to be addressed when tackling improving the air quality.

SUMMARY OF THE INVENTION

The present invention provides a complete system which allows each user to measure and improve the pollution footprint for that person's overall mobility, in a motorized vehicle and in soft modes of transport, using a simple application on a smart phone, known here as a smart phone application, without the need to add a specific sensor. This system is also of benefit to communities, allowing control of the levels of emissions for real usage, on their own territory.

The present invention supplements methods for the determination of pollution emissions of the prior art on a number of levels:

- by allowing the automatic detection of routes and modes of transport with deployment on a smart phone;
- by adding a downstream eco-driving component in order to take the driver's behavior into account;
- by optionally coupling with other models in order to control and simulate the efficacy of the road infrastructure and vehicle technologies.

With the invention it is possible to move from a simple model for determining pollution emissions from a given vehicle for a given route to a complete system for eco-driving and monitoring pollutants which does not require any sensors apart from a GPS. The principal advantage of such a solution is that it can be deployed on a large scale via a smart phone application. This application can be used to automatically detect the trips (soft mobility and motorized vehicle mobility), provide personalized guidance and qualify the "air quality" impact of the style of driving a motorized vehicle by use of an algorithm calculating the speed trajectory and the ideal polluting scores over a given route. The method in accordance with the invention may in particular be used to determine a target level for pollution emissions and provide guidance to the driver.

In addition, the invention is not limited to automobile or even motorized vehicles, and can be used to take into account mobility in a broad sense by considering use of alternative modes of transport (or soft modes of transport), by displaying environmental impact indicators of the overall mobility of the user and generating eco-mobility guidance.

The invention concerns a method for determining indicators regarding pollution caused by the overall mobility of a user, comprising steps of:

a. detecting trips in soft modes of transport and trips in motorized vehicles by use of a smart phone in to measure at least one of position, altitude and speed of the user;

b. determining a real environmental footprint linked to pollution emissions for each trip in a motorized vehicle by use of a model for estimating pollution emissions accounting for the macroscopic characteristics of the vehicle and a real speed profile representing a style of driving of the user;

c. determining a target environmental footprint from each of the motorized vehicle trips accounting for a target speed profile representing an optimal style of driving in the model for estimating pollution emissions;

d. breaking down the environmental footprint for each of the motorized vehicle trips into a footprint linked to a vehicle, a footprint linked to a style of driving and a footprint linked to a type of route;

e. determining an overall environmental footprint for mobility of a user accounting for all trips in soft modes of transport and trips in motorized vehicles over a given time interval, which preferably may be one day; and f. determining at least one of eco-driving indicators and environmental impact indicators for the user's overall mobility.

The environmental footprint for the motorized vehicle trip may be determined by aggregating all pollution emissions linked to local and global pollutants in a single benchmark, the benchmark being obtained by producing a weighted sum of emissions for each pollutant under consideration, the coefficients of the weighted sum being selected as a function of impact on health and environment.

The determination of the environmental footprint for the motorized vehicle trip may comprise a determination of pollution emissions linked to the motorized vehicle used by the user carried out by acquiring at least one macroscopic parameter relating to design of the vehicle, and by constructing of the vehicle:

i. a model of the vehicle which links at least one of position, altitude and speed of the vehicle to torque and speed of the engine using at least one macroscopic parameter;

ii. a model of the engine which links the torque and the speed of the engine to pollution emissions in exhaust from the engine by use of at least one macroscopic parameter; and iii. optionally, using a model of a post-treatment system which links the pollution emissions in exhaust from the engine by use of the pollution emissions in exhaust from the post-treatment system by use of at least one macroscopic parameter;

and by carrying out steps of:

measuring position, altitude and speed of the vehicle by use of a tracking system or a mobile phone;

determining the torque (Cme) and the speed (Ne) of the engine by means of the vehicle model and the measurements;

determining pollution emissions in exhaust from the engine by use of the engine model and the torque (Cme) and the speed (Ne) of the engine; and optionally, determining pollution emissions from the vehicle by use of the model of the post-treatment system and the pollution emissions in exhaust from the engine.

Preferably, the difference between a real environmental footprint and a target environmental footprint can be used to determine the environmental footprint linked to a style of driving of the user for each of the trips.

Advantageously, the difference between the real environmental footprint and the target environmental footprint can be used to determine an indicator of quality of a style of driving of the user in a form of a driving score.

Preferably, a potential for improvement for the user over the trip is determined.

The pollutants may be selected from at least one of carbon dioxide, greenhouse gases, oxides of nitrogen, particles, carbon monoxide and unburned hydrocarbons.

In one embodiment, the method may comprise a step for aggregating pollution emissions of different users or multiple transits by the same user over a route segment forming part of one of the motorized vehicle trips in order to estimate statistical distributions and mean levels of pollution emissions over the route segment.

The determination of the environmental footprint for the motorized vehicle trip may comprise a simulation of various engine technologies in order to evaluate real usage.

The invention also concerns a computer program product which can be downloaded from a communications network which is recorded on a not transient computer-readable medium which is executed by a processor or a server, comprising program code instructions for carrying out the method as described above, when the program is executed on a computer or on a mobile telephone.

Finally, the invention concerns using the method in order to estimate the ecological efficiency of a road infrastructure or road traffic restrictions.

The invention also concerns the use of the method in order to provide feedback of information to the user regarding the relative impact of each selected mode of transport within the environmental impact of his overall mobility, preferably in order to generate ecological improvement guidance for the overall mobility of the user.

BRIEF DESCRIPTION OF THE DRAWINGS

Other characteristics and advantages of the method in accordance with the invention will become apparent from the description below of non-limiting exemplary examples, made with reference to the accompanying figures and described below.

FIG. 2 which contains

DETAILED DESCRIPTION OF THE INVENTION

The invention can be used to produce a tool for managing and controlling impact of the overall mobility of a user on air quality. From a method for estimating pollution emissions, the method in accordance with the invention can be used to construct a complete solution deployable on a smart phone or on another system provided with a tracking sensor.

The method in accordance with the invention may be used to detect the mobility of the user in order to automatically feed data to models for estimating pollution emissions and also to provide indicators and guidance for eco-driving and/or eco-mobility from the pollution estimations.

The first step of the method ensures automatic detection of the mobility of the user as the user moves without involving prohibitive battery consumption, by using the various physical sensors present on a telephone (GNSS, GSM and inertial unit) to their utmost. This step for detecting mobility is indispensable so that models for estimating the pollution emissions can receive inputs.

An eco-driving component informs drivers about a portion of their emissions linked to their style of driving and helps them to reduce their emissions.

The complete solution can be used to determine indicators qualifying a polluting nature of mobility of a user by account for real trips as a whole:

by accounting for selected modes of transport (car, bicycle, walking, train, etc) in order to provide the user with feedback regarding relative environmental impact of each mode of transport; and by accounting for the user's style of driving in a case of car trips and providing for each route a portion of the emissions which the user could reduce by adjusting driving style, which constitutes the potential for improvement.

The method in accordance with the invention can also be used to display, over a given time interval, for example each day, the overall pollution footprint for the mobility of a user and to project these pollution levels onto a map.

Figure 1:
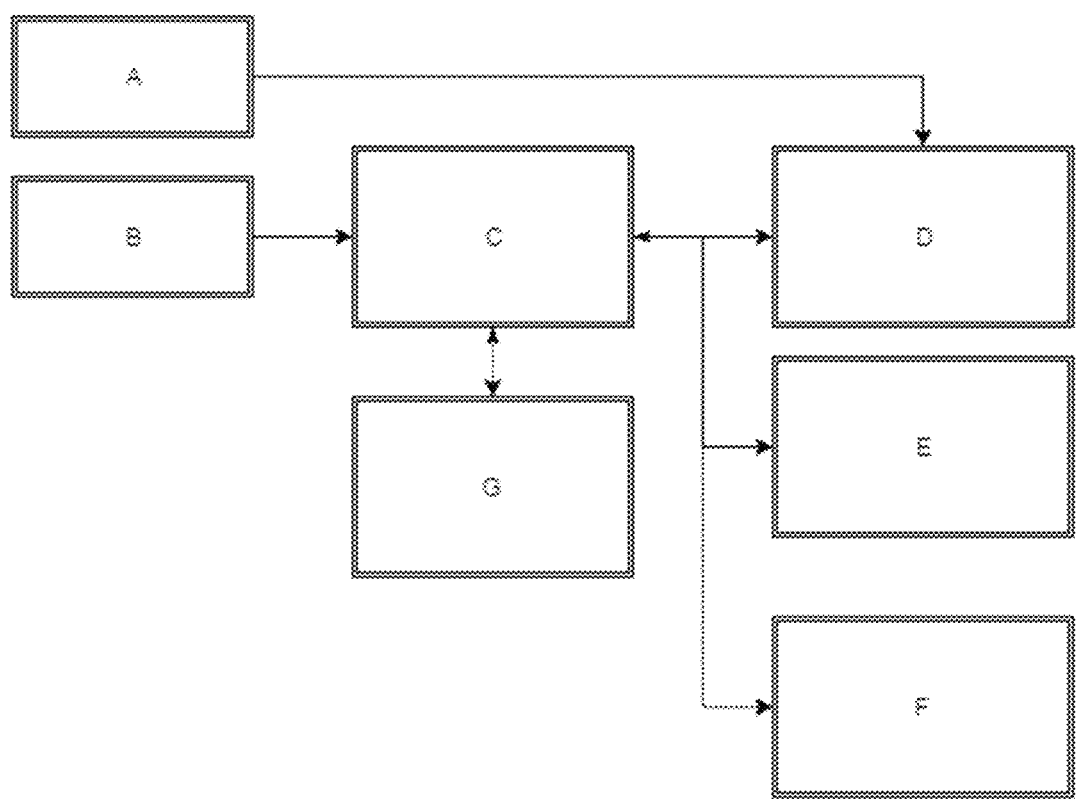
FIG. 1 illustrates the architecture of the method for determining eco-driving and eco-mobility indicators.
Figure 2A:
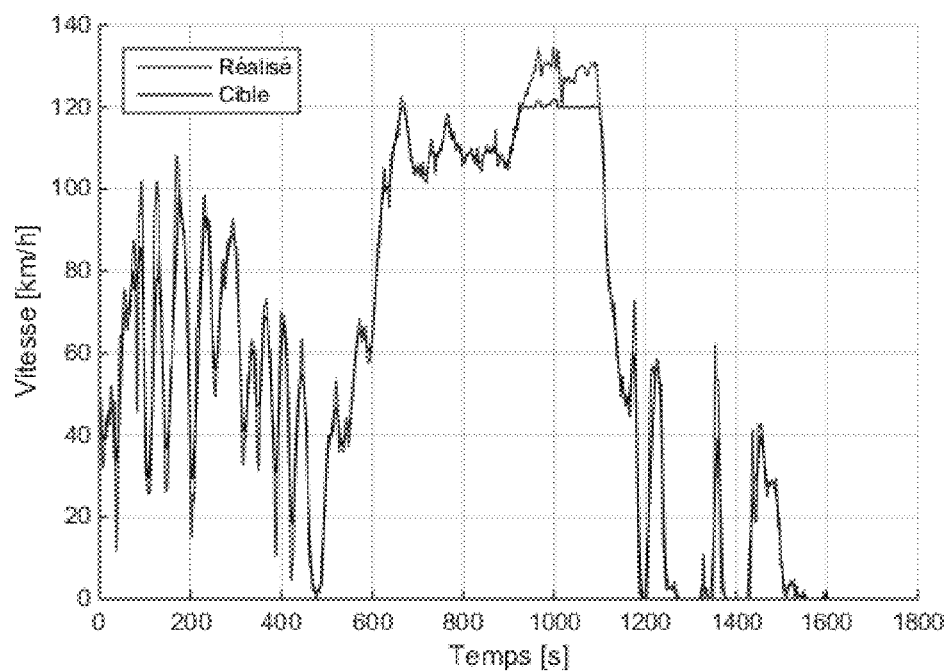
FIGS. 2A-2E illustrates Example 1 representing the potential for improvement to pollution emissions of NOx (FIG. 2C: instantaneous, FIG. 2E: cumulative) and consumption (FIG. 2B: instantaneous, FIG. 2D: cumulative) for a real speed profile, in relation to an increase in target speed, the profiles being represented in FIG. 2A for a given route and vehicle.
Figure 2B:
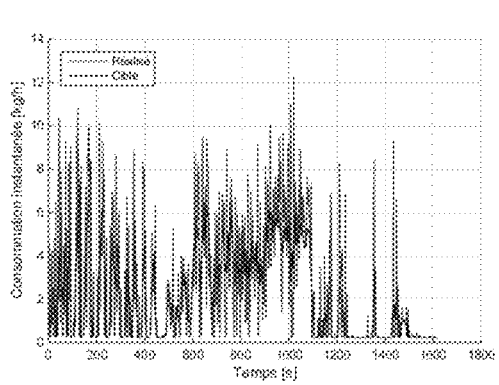
Figure 2C:
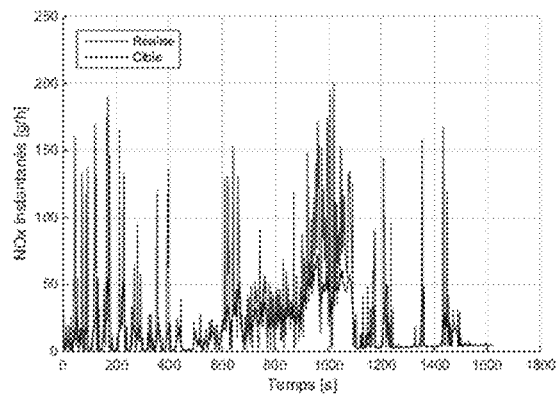
Figure 2D:
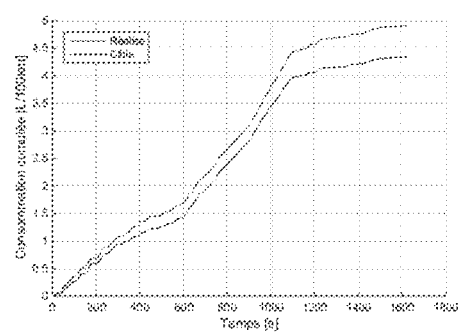
Figure 2E:
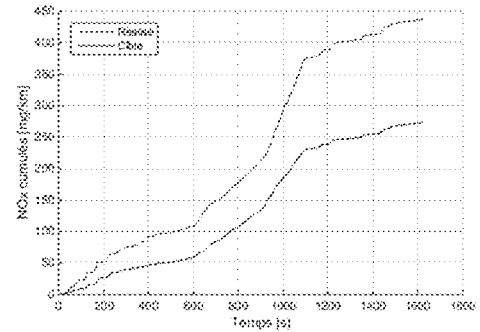

FIG. 1 illustrates the method in accordance with the invention by showing the architecture of the various steps of the method for determining indicators regarding the polluting nature of driving and of overall mobility:

A. detection of soft modes of transport
B. detection of trips in a motorized vehicle
C. determination of the environmental footprint for the motorized vehicle trip taking into account the style of driving
D. determining the overall environmental footprint for the mobility of the user over a given time interval, for example over a day, taking into account the footprint for soft mobility modes and the footprint linked to motorized vehicle trips
E. in the case of a route using a motorized vehicle, breaking down the environmental footprint for the route and determining eco-driving indicators for the user
F. optionally, aggregating pollution emissions estimated for each route segment
G. optionally, simulating various engine technologies in the determination of the environmental footprint for the motorized vehicle trip in order to evaluate real usage.

These various steps are detailed below.

A. Detection of Soft Modes of Transport

Soft modes of mobility, that is non-emitting, have to be taken into account when evaluating the environmental footprint for mobility, as they may be chosen as a substitute for polluting mobility solutions. Thus, in this regard, the soft modes of transport have to be recognized and encouraged. The method used means that automatic detection of walking, running and bicycle riding can be carried out because a smart phone is used or any other connected object, for example a connected wristwatch, and this being carried out by limiting battery consumption as much as possible. The method can thus be used to monitor the mobility of users of the system while requiring a minimum of intervention from them.

Because of the simple detection using an accelerometer, a magnetometer, or a gyroscope, for example, the trip is detected automatically and the mode of transport is identified. The output data obtained from this detection step are the mode of transport, the start time, the travel time and the distance covered.

B. Detection of Trips in a Motorized Vehicle

The method in accordance with the invention automatically detects, via a smart phone or any other connected object such as a connected wristwatch, trips in motorized vehicles by maximizing the sensitivity of detection at the start of each route and the accuracy of the collected data while limiting the battery consumption. The method does not require the constant use of tracking (GNSS). It is based on the observation of at least one of GSM antenna changes and the identification of the type of activity of the user detailed in the preceding section. When an antenna change is detected or the activity currently being detected is a motorized vehicle trip, for example in a car, the GNSS sensor of the smart phone is activated for a given period. If the recorded speed measurements correspond well to a speed representative of a motorized vehicle trip (when a motorized vehicle is being used), then recording of a fresh motorized vehicle trip is launched and the GNSS remains activated until the trip is finished. While travelling, the speed and altitude signals are recorded at all times, which means that the style of driving can intrinsically be taken into account. The end of the route is determined by the status of the speed. At the end of the route, the recorded data are sent to a server or are stored locally for subsequent onward transmission (in particular in the case in which there is no network at the end of the route).

The identification of the motorized vehicle used for each trip may be carried out either by reporting to the user, or by automatically comparing the route followed with certain known routes (tramway, bus, glider, etc).

Matching with a road map, known as "map matching", which consists of projecting points from the GPS trace (latitude and longitude) onto a map and, by means of an optimization algorithm, placing them if necessary onto the closest route, is used to:

correct the recorded coordinates by repositioning the positions on the routes identifying certain types of trip in a motorized vehicle, in particular city buses.

Route fusion is a method for aggregating several routes recorded over a given time period and which have to be considered as one and the same route.

C. Determination of the Environmental Footprint of a Trip Taking into Account the Style of Driving The emissions of various pollutants generated for each motorized vehicle trip are aggregated into a single benchmark in order to provide an indicator which is intelligible and easy to follow over time. For each route j carried out using a vehicle k, a value $POPS_{j,k}$ is determined by producing the weighted sum of the cumulative emissions for each pollutant i. The various pollutants are taken into account in proportion to their danger level. The weighted factors $\alpha_i$ for the various pollutants may be calculated using the external cost method (state of the art in the measurement of societal impact). These factors reflect the danger level of each pollutant and are independent of the vehicle.

$$POPS_{j,k} = \sum_i \alpha_i \times \phi_{i,j,k}^{[\frac{g}{km}]}$$

A non-exhaustive list of the pollutants considered is given below:

carbon dioxide, a greenhouse gas
oxides of nitrogen
carbon monoxide
fine particles
unburned hydrocarbons
sulphur dioxide In the case of shared transport (public transport or car sharing), a weighting may be applied in order to normalize the emissions to the number of users.

The cumulative emissions $$\phi_{i,j,k}^{[\frac{g}{km}]}$$

for each pollutant i over the route j with the vehicle k are calculated by integrating the instantaneous emissions over the route $$\psi_{i,j,k}^{[\frac{g}{h}]}(t),$$

which are themselves calculated using pollutant models which are known in the prior art, such as those detailed in patent application FR 3 049 653, for example. From a macroscopic point of view, this calculation can be expressed by the following equations:

$$\begin{cases} \phi_{i,j,k}^{[\frac{g}{km}]} = \int_{t_i}^{t_f} \psi_{i,j,k}^{[\frac{g}{h}]}(t)dt \\ \psi_{i,j,k}^{[\frac{g}{h}]}(t) = f_k(V_j(t), Alt_j(t), T_j(t), spec_k) \end{cases}$$

in which:
- $V_j(t)$ is the vehicle speed and $Alt_j(t)$ are the speed and altitude profiles measured by the GNSS over the route j
- $T_j(t)$ is the outside temperature, recalculated from the GNSS coordinates
- $f_k$ is the model used for the vehicle k, and $spec_k$ are the technological specifications for the vehicle used to parameterize the models which are, for example:
  - the type of engine (gasoline, diesel, etc)
  - the level of the certification standard (Euro 1, Euro 2, ...)
  - the number of cylinders
  - the maximum torque and the associated engine speed
  - the maximum power and the associated engine speed
  - the mass of the vehicle
  - the type of vehicle transmission
  - the type of post-treatment system
  - the type of injection system
  - the degree of hybridization D. Determination of the Overall Environmental Footprint for the Mobility Over a Given Time Interval, for Example a Day The set of pollutant footprints generated by each of the trips over a given time interval, for example during the course of a day (irrespective of the mode), are aggregated in order to provide a single indicator over the time interval. This aggregation is carried out by calculating a mean weighted by the distances covered during each route, $d_j^{[km]}$, using the following formula, for example for one day:

$$POPS_{day} = \frac{\sum_j d_j^{[km]} * POPS_{j,k}}{\sum_j d_j^{[km]}}$$

This determination of the overall environmental footprint for the mobility can be used to estimate the environmental impact for the overall mobility of the user. This determination may also be used to generate eco-mobility guidance by demonstrating the trips responsible for high levels of emissions and to provide guidance which is applicable to the driver in order to eliminate or reduce them. The aim is to promote modes of transport which do not produce emissions by providing the user with a potential for improvement to his overall mobility. As an example, for a very short route or for a route which follows a bus line, guidance may also be given to the user to indicate the savings which could have been obtained by taking public transport or by using a non-emissive mode of transport such as walking or using a bicycle.

E. Breaking Down the Environmental Footprint for the Trip and Determination of Eco-Driving Indicators for the User Because of the current rules for calibrating engine control strategies and physical phenomena, the level of pollution emissions is very sensitive, far more than consumption, to the conditions of use of style of driving and type of route.

In real usage, the emissions from the same vehicle can vary significantly and the present method is particularly aimed at breaking down the overall footprint $POPS_{j,k}$ into three portions, linked to the vehicle, the style of driving and the type of route:

$$POPS_{j,k} = POPS_{veh}(k) + POPS_{drive}(j,k) + POPS_{route}(j,k)$$

Footprint Linked to the Vehicle $POPS_{veh}(k)$

The environmental footprint for a vehicle is closely linked to the technologies employed (type of fuel, type of decontamination system, etc) and to the standard to which it adheres. Over a very low emissions reference route and with a nominal style of driving, the environmental footprint represents the minimum emissions from a vehicle for ideal usage. For each pollutant i, the vehicle footprint, expressed in grams per kilometer, is determined with the aid of a pollution emissions calculation as described above, taking into account the speed $V_{cycle\ ref}$ and the altitude $Alt_{cycle\ ref}$ of a real reference run corresponding to a low-emissions route and style of driving.

$$\begin{cases} POPS_{veh}(k) = \sum_i \alpha_i \times \phi_{i,cycle\ ref,k}^{[\frac{g}{km}]} \\ \phi_{i,cycle\ ref,k}^{[\frac{g}{km}]} = \int_{t_i}^{t_f} \psi_{i,cycle\ ref,k}^{[\frac{g}{h}]}(t)\ dt \\ \psi_{i,cycle\ ref,k}^{[\frac{g}{h}]}(t) = f_k(V_{cycle\ ref}(t), Alt_{cycle\ ref}(t), T_{cycle\ ref}(t), spec_k) \end{cases}$$

Footprint Linked to Style of Driving $POPS_{drive}(j, k)$

The method described below evaluate the quality of the style of driving by determining the target environmental footprint for the route being studied and thus the potential for improvement. As detailed below, the goal is to demonstrate driving behavior responsible for high levels of emissions and to provide guidance applicable to the driver in order to eliminate them. The approach is based on the instantaneous speed measured and the characteristics of the vehicle.

$$V_{cycle\ target}(t) = f_j(V_{cycle\ real}(t), spec_k)$$

Starting from the speed profile produced and the technical specifications of the vehicle, the method $f_j$ determines a target speed profile by:
- applying maximum acceleration thresholds: these thresholds may be constant or dependent on the speed and depend on the characteristics of the vehicle;
- determining a limiting maximum speed;
- improving speed maintenance and anticipating braking by filtering the speed profile.

The goal of the method is that the modifications applied to the speed profile should be intelligible to the driver to permit conversion into practical guidance which can be directly applied by the driver.

Each of the speed profiles, real and target, are used as an input for the same model of pollution emissions $\eta_k$ used for the vehicle k, in order to determine, respectively, the real and target pollution footprints:

real footprint for route:

$$\begin{cases} POPS_{cycle\ real}(j,k) = \sum_i \alpha_i \times \phi^{[\frac{g}{km}]}_{i,cycle\ real,k} \\ \phi^{[\frac{g}{km}]}_{i,cycle\ real,k} = \int_{t_i}^{t_f} \psi^{[\frac{g}{h}]}_{i,cycle\ real,k}(t)\,dt \\ \psi^{[\frac{g}{h}]}_{i,cycle\ real,k}(t) = f_k(V_{cycle\ real}(t), Alt_{cycle\ real}(t), T_{cycle\ real}(t), spec_k) \end{cases}$$

target footprint for route:

$$\begin{cases} POPS_{cycle\ target}(j,k) = \sum_i \alpha_i \times \phi^{[\frac{g}{km}]}_{i,cycle\ target,k} \\ \phi^{[\frac{g}{km}]}_{i,cycle\ target,k} = \int_{t_i}^{t_f} \psi^{[\frac{g}{h}]}_{i,cycle\ target,k}(t)\,dt \\ \psi^{[\frac{g}{h}]}_{i,cycle\ target,k}(t) = f_k(V_{cycle\ target}(t), Alt_{cycle\ target}(t), T_{cycle\ target}(t), spec_k) \end{cases}$$

The difference between the real and target environmental footprint can be used to determine the footprint linked to the style of driving, and thus the potential for improvement over this route:

$$POPS_{drive}(j,k) = POPS_{cycle\ real}(j,k) - POPS_{cycle\ target}(j,k)$$

Knowing this portion of the footprint due to the style of driving permit an indicator of the quality of the style of driving to be determined:

$$\text{Driving score} = f(POPS_{drive}(j,k), POPS_{j,k}, spec_k)$$

Footprint Linked to Route $POPS_{route}(j,k)$

The target environmental footprint for the route thus represents the environmental footprint which can be attained with an optimal style of driving. The difference between this footprint and the reference footprint for the vehicle can then be attributed to the type of the route itself: short routes which are not favorable to the efficiency of decontamination systems, busy routes or freeway routes which are highly energy-consuming, steep inclines:

$$POPS_{route}(j,k) = POPS_{cycle\ target}(j,k) - POPS_{veh}(k)$$

The portion linked to the route also depends on the type of vehicle, because various vehicle technologies do not have the same sensitivity to the conditions of the run. As an example, a vehicle provided with a "Stop/Start" system will be penalized less in heavily congested traffic.

F. Aggregation of Pollution Emissions over Each Segment of the Route

In the case in which the pollution emission profiles are tracked (latitude and longitude recorded), it is possible to project them onto a map and aggregate the emissions from different users or multiple transits by the same user. This means that statistical distributions and mean pollution emission levels can be estimated for each segment of the route. Thus, for example, it becomes possible to add critical zones for pollution emissions to the map, with the goal of providing dynamic feedback of information regarding the environmental efficacy of the road infrastructure and the associated restriction. This is an added benefit of the present invention both to the public at large, and also to communities or businesses.

G. Simulation of Different Engine Technologies in Order to Evaluate Real Usage

In the case of the principal application of the system of the present invention, the pollution models which represent the engine and vehicle technologies are parameterized in order to be representative of vehicles actually used during trips, since the goal is to estimate real usage emissions to the best extent possible.

However, there is an alternative application of the system in which the models could be configured in order to simulate other vehicles or simply other engine configurations, with the goal of carrying out simulation studies. Two examples may be cited:

simulating emissions from a given fleet of vehicles (different from the real fleet) in order to evaluate the efficiency of different traffic trip policies during peaks of pollution or to carry out projections of emission levels in future years. Compared with methods in current use for such studies, the present invention has the advantage of accounting for the run conditions for real usage (speed and inclination profiles recorded)

simulating emissions with vehicles provided with novel technological engine modules in order to evaluate the efficiency in real usage of novel technologies on reducing pollution emissions.

Advantages of the Invention

Compared with prior art methods for estimating pollution emissions, the method in accordance with the invention has a number of advantages, in particular:

The method in accordance with the invention can be used to monitor local and overall pollution emissions by automotive transport, by use of a solution which can be deployed on a large scale and at low cost via the use of smart phones.

The method in accordance with the invention can be used to guide the driver in order to assist reduction of the driver's pollution footprint linked to motorized vehicle trips, by improving style of driving by determining an environmental footprint and breaking the footprint down into three factors: car, driving and route.

The method in accordance with the invention can be used to guide the user assist reduction of pollution footprint by improving the user's modes of transport.

The method in accordance with the invention can account for the real overall mobility of the user by selection of the mode of transport and style of driving.

The method in accordance with the invention can be used to aggregate local and overall pollution into a single benchmark with coefficients which are representative of the impact of each pollutant on health and on the environment.

The method also makes it possible to determine an overall footprint of the mobility of the user over a given time interval, for example every day, by accounting for all modes of transport used (soft or in a motorized vehicle).

The method can be used to quantify, in a precise manner, the potential for improvement linked to the style of driving of the user for a trip carried out with a given vehicle.

The ecological nature of driving is quantified, not simply with respect to the consumption of fuel or $CO_2$, but in an overall benchmark for local and overall pollution.

The method can also be used to detect all of the trips of a user and to identify the mode of transport used without any other sensor apart from a smart phone or any other connected object, such as a connected wristwatch, and all while limiting battery consumption.

The method can be used to record, over a trip, the data necessary for determining the environmental footprint for that trip.

EXAMPLES

Example 1

Example 1 below illustrates a real case of breaking down the pollution footprint determined for each motorized vehicle trip as well as the determination of the potential for improvement. By generating a target speed profile representative of an optimal style of driving, the method in accordance with the invention can be used to precisely quantify the potential for improvement linked to the style of driving for a route travelled with a given vehicle. FIG. 2 illustrates a comparison between a generated target speed profile and a real speed profile for the same route (FIG. 2A) and the potential savings in fuel consumption (instantaneous in kg/h FIG. 2B, and cumulative in L/100 km, FIG. 2D) and oxides of nitrogen emissions (instantaneous in g NOx/h in FIG. 2C, and cumulative emissions in mg NOx/km, FIG. 2E) as a function of time (in s) for a diesel vehicle. It will be observed that it is possible to significantly reduce pollution emissions with minor modifications to the way of driving. Thus, in the above example, a saving in consumption of 9.8% and a reduction in NOx emissions of 31.4% could be obtained if the driver approached an optimal style of driving. This constitutes the potential for improvement which is communicated to the driver by the system carrying out the method in accordance with the invention, directly or to his smart phone.

Example 2

Figure 3:
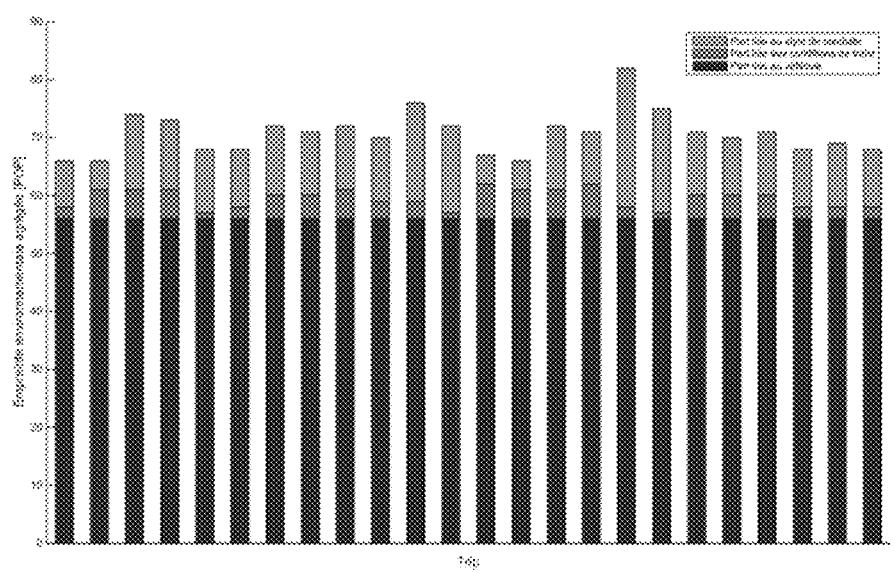
FIG. 3 illustrates Example 2 representing a break down of factors impacting the pollution emissions during a study carried out on real runs travelled over the same route with the same motorized vehicle and different drivers.

Example 2 illustrates the breakdown of factors having an impact on pollution emissions for 24 different users driving the same vehicle over the same route. FIG. 3 represents, in the form of histograms, the aggregated environmental footprint broken down into a portion linked to style of driving, a portion linked to the route conditions and a portion linked to the vehicle, as a function of the driver. This figure illustrates the function of the algorithm which can be used to determine the portion of pollution emissions linked to the style of driving in the overall pollution footprint (aggregated environmental footprint, POP). In fact, for the same route and the same vehicle, it will be observed that the pollution level varies substantially as a function of the driver. However, the difficulty is to estimate, from a single transit, whether there is a potential for improvement to the pollution emissions linked to improving the style of driving. It will be observed that for different repetitions of the same route that:

The portion linked to the vehicle does not vary, because the vehicle is not changed;

The portion linked to the route does not vary much, because the itinerary followed is the same, but the run conditions are never strictly reproducible (traffic, stop lights, etc);

The portion linked to the style of driving varies significantly and it will be observed that the sum of the portion linked to the route and the portion linked to the vehicle varies only slightly, which shows that the algorithm is extremely capable of successfully estimating the potential for reducing emissions, and thus the potential for improvement by the user as regards the user's style of driving.

The invention claimed is:

1. A method for determining indicators regarding a nature of pollution of overall mobility of a user, comprising:
   a. detecting trips in soft modes of transport and trips in a motorized vehicle by use of a smart phone to measure at least one of position, altitude and speed of the user;
   b. determining an environmental footprint linked to pollution emissions for each trip in a motorized vehicle by use of a model which estimates pollution emissions by accounting for macroscopic characteristics of the vehicle and a speed profile representing a style of driving of the user;
   c. determining a target environmental footprint from each of the motorized vehicle trips by accounting for a target speed profile representing an optimal style of driving in the model for estimating pollution emissions;
   d. breaking down the environmental footprint for each of the motorized vehicle trips into a footprint linked to the motorized vehicle, a footprint linked to style of driving and a footprint linked to a type of route;
   e. determining an overall environmental footprint for the mobility of the user by accounting for all trips in soft modes of transport and trips in motorized vehicles over a given time interval; and
   f. determining at least one of eco-driving indicators and environmental impact indicators for the user's overall mobility.

2. The method as claimed in claim 1, wherein the environmental footprint for each motorized vehicle trip is determined by aggregating all pollution emissions linked to local and global pollutants in a single benchmark, the benchmark being obtained by producing a weighted sum of the emissions for each pollutant under consideration, with coefficients of the weighted sum being selected as a function impact on health and environment.

3. The method as claimed in claim 1, wherein determination of the environmental footprint for the motorized vehicle trips comprises a determination of pollution emissions linked to a motorized vehicle being used by the user is determined by acquiring at least one macroscopic parameter relating to design of the vehicle, and by constructing for the vehicle:
   i. a model of the vehicle linking at least one of position, altitude and speed of the vehicle to torque and speed of the engine by use of at least one macroscopic parameter;
   ii. a model of the engine linking torque and speed of the engine to pollution emissions in exhaust from the engine by use of at least one macroscopic parameter; and
   iii. a model of the post-treatment system linking pollution emissions in exhaust from the engine by use of the pollution emissions in the exhaust from the post-treatment system by use of at least one macroscopic parameter;

and by carrying out the following steps:
   a) measuring position, altitude and speed of the vehicle by use of a tracking system or a mobile phone;

b) determining torque and speed of the engine by use of the vehicle model and the measurements;

c) determining pollution emissions in the exhaust from the engine by use of the engine model and the torque and the speed of the engine; and d) determining pollution emissions from the vehicle by use of the model of the post-treatment system and the pollution emissions in exhaust from the engine.

4. The method as claimed in claim 2, wherein determination of the environmental footprint for the motorized vehicle trips comprises a determination of pollution emissions linked to a motorized vehicle being used by the user is determined by acquiring at least one macroscopic parameter relating to design of the vehicle, and by constructing for the vehicle:

i. a model of the vehicle linking at least one of position, altitude and speed of the vehicle to torque and speed of the engine by use of at least one macroscopic parameter;

ii. a model of the engine linking torque and speed of the engine to pollution emissions in exhaust from the engine by use of at least one macroscopic parameter; and iii. a model of the post-treatment system linking pollution emissions in exhaust from the engine by use of the pollution emissions in the exhaust from the post-treatment system by use of at least one macroscopic parameter;

and by carrying out the following steps:

a) measuring position, altitude and speed of the vehicle by use of a tracking system or a mobile phone;

b) determining torque and speed of the engine by use of the vehicle model and the measurements;

c) determining pollution emissions in the exhaust from the engine by use of the engine model and the torque and the speed of the engine; and d) determining pollution emissions from the vehicle by use of the model of the post-treatment system and the pollution emissions in exhaust from the engine.

5. The method as claimed in claim 1, in wherein a difference between a real environmental footprint and a target environmental footprint is used to determine an environmental footprint linked to a style of driving by the user for each of the trips.

6. The method as claimed in claim 2, in wherein a difference between a real environmental footprint and a target environmental footprint is used to determine an environmental footprint linked to a style of driving by the user for each of the trips.

7. The method as claimed in claim 3, in wherein a difference between a real environmental footprint and a target environmental footprint is used to determine an environmental footprint linked to a style of driving by the user for each of the trips.

8. The method as claimed in claim 4, in wherein a difference between a real environmental footprint and a target environmental footprint is used to determine an environmental footprint linked to a style of driving by the user for each of the trips.

9. The method as claimed in claim 5, wherein a difference between the real environmental footprint and the target environmental footprint is used to determine an indicator of quality of the style of driving of the user in a driving score.

10. The method as claimed in claim 5, comprising determining a potential for improvement for the user over the trip.

11. The method as claimed in claim 9, comprising determining a potential for improvement for the user over the trip.

12. The method as claimed in claim 1, wherein pollutants are at least one of carbon dioxide, greenhouse gases, oxides of nitrogen, particles, carbon monoxide and unburned hydrocarbons.

13. The method as claimed in claim 1, comprising aggregating pollution emissions for different users or multiple transits by a same user over a route segment forming part of one of the motorized vehicle trips to estimate statistical distributions and mean levels of the pollution emissions over the route segment.

14. The method as claimed in claim 2, comprising aggregating pollution emissions for different users or multiple transits by a same user over a route segment forming part of one of the motorized vehicle trips to estimate statistical distributions and mean levels of the pollution emissions over the route segment.

15. The method as claimed in claim 3, comprising aggregating pollution emissions for different users or multiple transits by a same user over a route segment forming part of one of the motorized vehicle trips to estimate statistical distributions and mean levels of the pollution emissions over the route segment.

16. The method as claimed in claim 5, comprising aggregating pollution emissions for different users or multiple transits by a same user over a route segment forming part of one of the motorized vehicle trips to estimate statistical distributions and mean levels of the pollution emissions over the route segment.

17. The method as claimed in claim 9, comprising aggregating pollution emissions for different users or multiple transits by a same user over a route segment forming part of one of the motorized vehicle trips to estimate statistical distributions and mean levels of the pollution emissions over the route segment.

18. The method as claimed in claim 1, wherein a determination of the environmental footprint for the motorized vehicle trip comprises simulating engine technologies to evaluate real engine usage.

19. A computer program product which is recorded with a tangible computer-readable storage medium comprising program code instructions for carrying out the method as claimed in claim 1, when the program is executed on a computer or on a mobile telephone.

20. The method as claimed in claim 1, used for estimating ecological efficiency of a road infrastructure or road traffic restrictions, comprising projecting and aggregating emissions from users or from multiple transits by a same user onto a map to estimate statistical distributions and mean levels of pollution emissions for each segment of the route; and marking the map with zones of pollution emissions in dynamic feedback information regarding environmental efficiency of road infrastructure and associated restrictions.

* * * * *